United States Patent [19]

Hartmann

[11] 4,101,278

[45] Jul. 18, 1978

[54] IONIZATION DETECTOR UTILIZING TRITIATED SCANDIUM WITH AN ACCEPTABLE TRITIUM EMANATION RATE AT HIGH TEMPERATURE

[75] Inventor: Charles Harold Hartmann, Moraga, Calif.

[73] Assignee: Varian Associates, Inc., Palo Alto, Calif.

[21] Appl. No.: 396,921

[22] Filed: Sep. 13, 1973

Related U.S. Application Data

[62] Division of Ser. No. 232,016, Mar. 6, 1972, abandoned.

[51] Int. Cl.$^2$ .............................................. G01N 31/08
[52] U.S. Cl. ................................. 23/232 C; 23/254 R;
    55/386; 73/23.1; 75/122.5; 148/20.3; 210/31 C;
    250/381; 250/384
[58] Field of Search ............. 23/232 C, 232 R, 254 R;
    250/302, 303, 304, 336, 375, 379, 381, 384;
    210/31 C; 55/386

[56] References Cited

U.S. PATENT DOCUMENTS

| | | | |
|---|---|---|---|
| 3,185,845 | 6/1965 | Lively et al. | 250/304 |
| 3,601,609 | 8/1971 | Yauger | 250/375 |
| 3,725,009 | 4/1973 | Lovelock | 23/232 C |

OTHER PUBLICATIONS

Fenimore et al., *Analytical Chem.*, v. 43, pp. 1972-1975 (1971).
Hartmann, *Analytical Chem.*, v. 45, pp. 733-739 (1973).

*Primary Examiner*—Sidney Marantz
*Attorney, Agent, or Firm*—Stanley Z. Cole; John J. Morrissey; Gerald M. Fisher

[57] ABSTRACT

An ionization detector, such as an electron capture detector for use in pesticide residue analysis, utilizes a scandium tritide beta particle source. The scandium tritide forms a surface portion of a metallic foil. If the foil initially exhibits an unacceptably high tritium emanation rate at desired high operating temperatures, e.g., at temperatures above 250° C, the foil can be treated so as to exhibit an acceptable tritium emanation rate at such temperatures. The treatment comprises heating the foil at a predetermined treatment temperature, e.g., at a selected temperature in the 300° to 400° C range, until the tritium emanation rate for the foil at the selected treatment temperature reaches a value which correlates with an acceptable tritium emanation rate for the foil at a particular desired operating temperature.

4 Claims, 3 Drawing Figures

IONIZATION DETECTOR UTILIZING TRITIATED SCANDIUM WITH AN ACCEPTABLE TRITIUM EMANATION RATE AT HIGH TEMPERATURE

This is a division of application Ser. No. 232,016 filed Mar. 6, 1972, now abandoned.

BACKGROUND OF THE INVENTION

Certain forms of ionization detectors measure ionization of gaseous matter within a gas chamber into which a sample gas is delivered, utilizing a radiation source producing beta emission for the ionization of the sample. Such beta emitters find use in electron capture detectors and helium ionization detectors; for example, electron capture detectors are widely used in the field of pesticide residue analysis.

These prior detector cells typically contained a radioactive source such as $Ti^3H$ or $^{63}Ni$ as the internal beta emitter. Although the $^{63}Ni$ emitter has a lower emitter activity, hence a lower sensitivity and smaller linear range, and a higher cost than the well known $Ti^3H$ source, it has a distinct advantage in use with detectors for operation at relatively high temperatures.

As explained in U.S. Pat. No. 3,601,609, issued Aug. 24, 1971 to W. L. Yauger, entitled "Ionization Detection Device Using A Nickle-63 Radioactive Source", the United States Atomic Energy Commission limits the temperature of operation of detectors using tritiated foils as a source to operating temperatures of about 220°–225° C since tritium emanation from such tritiated foil sources reaches unacceptable levels above this temperature. However, oftentimes it is desirable to operate the detector at a much higher temperature. For example, electron capture detectors are widely used in the field of pesticide residue analysis requiring such higher temperatures. However, the AEC has imposed temperature limit of about 220° C, which causes chronic condensation contamination of the foil source during use. This condensation is very deleterious to performance since the tritiated foils are low energy beta emitters and any obstruction will seriously inhibit the radioactive ionization of the sample gases. For this reason, it is desirable to operate at temperatures above 250° C, for example at 350° C. This higher temperature operation is permitted by the AEC with the expensive $^{63}Ni$ sources, whereas the use of tritium ($^3H$) emitters has been heretofore forbidden due to their excessive tritium emanation rate at such high temperatures.

SUMMARY OF THE PRESENT INVENTION

In the present invention, a novel process is described for treating scandium tritide beta particle sources intended for use as beta emitters in ionization detectors, these treated sources providing acceptable tritium emanation levels at elevated operating temperatures, i.e. at temperatures above 250° C. The process comprises the step of preliminarily heating the scandium tritide under controlled radiation precautions at a treatment temperature above 250° C, for example at 300° C., for a sufficient time period, for example 2 to 16 hours, to drive off excess radioactive material, i.e., tritium, until such time as the tritium emanation decays to an acceptable radiation level. Since the AEC has decreed that the tritium emanation from a standard 250 mCi $Ti^3H$ source at or below 220° C is at an acceptable radiation level, this radiation level may be arbitrarily selected as the desired and acceptable level and can conveniently be employed as a standard tritium emanation level. Thus the emanation ratio, which is defined as the ratio of the measured tritium emanation rate to the tritium emanation rate at 220° C, is a simple dimensionless number for comparing beta sources, emanation ratios of 1 or less being within the standards of the AEC. This technique of preliminary heat treatment, renders scandium tritide ($Sc^3H$) beta particle sources suitable for operation at high temperatures with acceptable tritium emanation rates, i.e., with emanation ratios of 1 or less.

DESCRIPTION OF THE PREFERRED EMBODIMENTS

Figure 1:
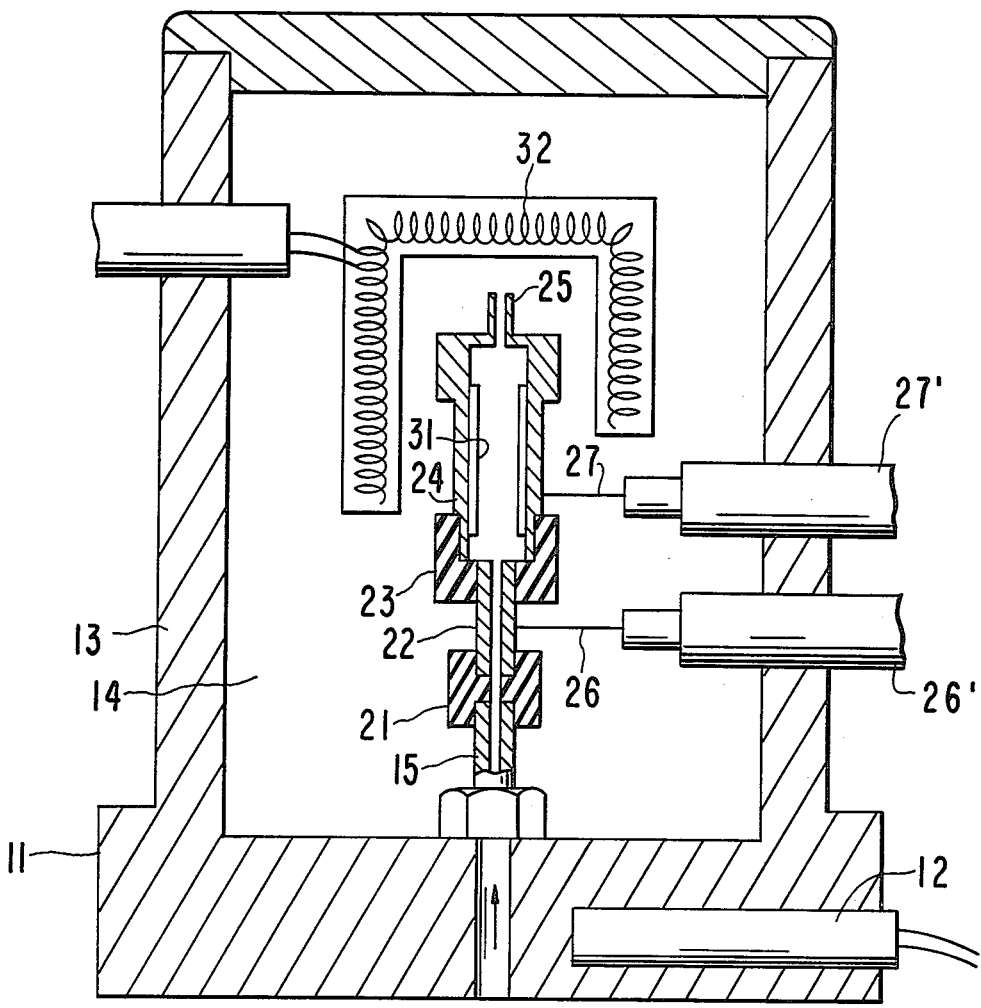
FIG. 1 is a longitudinal cross-sectional view of an electron capture detector utilizing the novel radiation source of the present invention.

Referring now to the drawing, the electron capture detector assembly shown in FIG. 1 comprises a mounting base 11 having a base heater 12 therein and a body envelope 13 surrounding the chamber 14 in which the detector cell is mounted. The cell comprises a hollow stainless steel input tubing 15 mounting the cell on the base 11 and through which the gas to be analyzed is introduced into the cell.

A first hollow cylindrical ceramic tubing 21 is vacuum sealed at one end to the inner end of the input tubing 15, and vacuum sealed at the other end to a hollow cylindrical stainless steel tube 22 forming the collector electrode or anode. A second hollow cylindrical, cup-shaped ceramic tubing 23 is vacuum sealed to the other end of the collector electrode 22 and is also vacuum sealed to the lower end of a hollow cylindrical stainless steel polarization electrode or cathode 24. The upper end of the polarization electrode 24 is provided with an exhaust tubing 25.

Electrical leads 26 and 27 extend through suitable insulators 26' and 27' in the side of envelope 13 and couple to the associated collector and polarization electrodes for providing the desired steady state or pulsed DC potential in the range of 0 to 90 volts across the anode and cathode electrodes during use.

A tritiated foil 31 is positioned around the inner wall of the polarization electrode 24. A heater coil 32 is mounted on the body envelope 13 and extends around the polarization electrode portion of the detector cell for raising the temperature of this reaction region of the cell to the desired operating temperature, for example 250°–350° C.

In operation of this electron capture detector with the output from a gas chromatograph, beta emission from the radiation source 31 results in an ionization of the carrier gas, either $N_2$ or Ar plus about 10% methane quenching gas, to form an electron flow in the detector cavity in the order of $10^{-8}$ amperes. The background current or standing current formed by the electron is collected by the relative weak field strength of the potential across the anode and cathode. Those substances in the gas which have an affinity for free electrons deplete the standing current as they pass through the cell from input to exhaust. The magnitude of the current depletion is a measure of the amount of capturing species in the detector, and is also a measure of the electron affinity of the species.

Tritiated ($Ti^3H$) foil has been widely used in the past as the radioactive source for ionization (usually detectors 250 mCi $^3H$) a standard. The tritium would typically be occluded in a suitable substrate, usually titanium plated on a stainless steel foil. When operated at high temperatures, for example above 220° C, the untreated $Ti^3H$ produces an unacceptable level of tritium emanation as determined by the U.S. Atomic Energy Commission, where emanation refers to the release rate of the tritium gas expressed in its radioactive equivalent, typically $\mu Ci/min$. However, often it is desired to operate above 220° C to prevent contamination of the radioactive source as stated above, and for this reason $^{63}Ni$ had previously been required.

Figure 2:
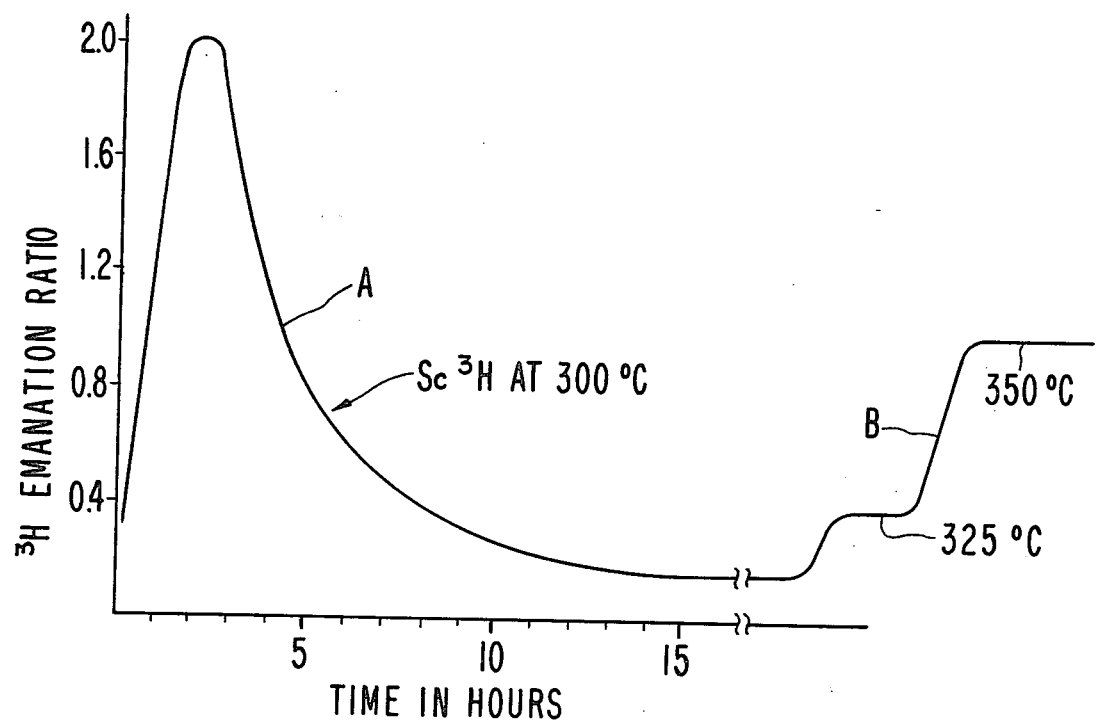
FIG. 2 illustrates graphically how the tritium emanation ratio of a $Sc^3H$ beta radiation varies with time during heat treatment at 300° C, and during subsequent operation at temperatures of 325° and 350° C.

It has been discovered that a heat treatment will condition a scandium tritide coated foil so that subsequent operation at other, either higher or lower, temperatures will yield an acceptable $^3H$ emanation rate. For example, and referring to FIG. 2, a scandium tritide foil was obtained from the manufacturer, U.S. Radium Corporation of Bloomsburgh, Pennsylvania, specified as 250 mCi of tritium. If this foil were to be placed directly in an electron capture detector without first being heat treated according to this invention, and if such detector were to be operated at a relatively high operating temperature, for example 325° C, the tritium emanation therefrom would exceed the legally acceptable level. However, if this foil is first heated at 300° C the tritium emanation therefrom, as can be seen from the curve A which shows emanation ratio vs. time, will reach a peak value of about 2 at about two hours and then will decay to a substantial equilibration value of about 0.16 after about 14 hours. After this heat treatment, the same foil may be operated at higher temperature levels without exceeding an acceptable tritium emanation level. This is illustrated by curve B which shows a subsequent operation of this foil at 325° C with an emanation ratio of 0.4, and a still further operation of this foil at 350° C with an emanation ratio of 1. Thus, since one arbitrarily selects as an acceptable emanation ratio, this heat treated foil may be used with operating temperatures up to 350° C.

Figure 3:
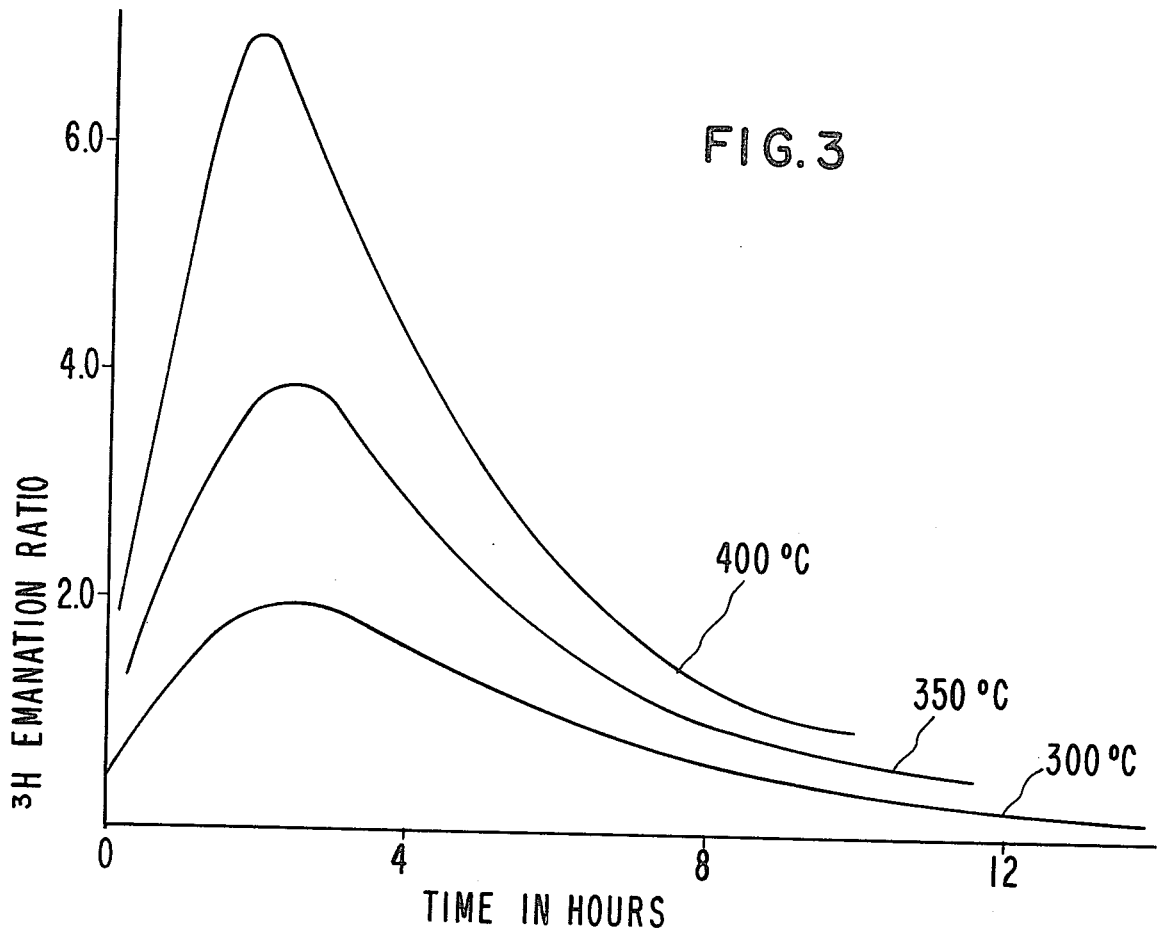
FIG. 3 illustrates graphically how the tritium emanation ratio of a $Sc^3H$ beta radiation source varies with time for three different heat treatment temperatures.

Different heat treatments yield different treatment results, as illustrated by the curves in FIG. 3 for three different $Sc^3H$ foils. The end points of all three of the treatments illustrated show acceptable emanation ratio. The lower temperature of 300° C required about 14 hours to each equilibration with relatively low percentage of $^3H$ loss during the process (calculated from the area under the emanation ratio curve). The higher temperature treatment of 400° C required a shorter time to reach equilibration, about 10 hours, but with relatively higher percentage of $^3H$ loss and shorter useable life expectance when the source is actually employed in the detector process of a gas chromatograph. It is not required that equilibration of the $^3H$ emanation be reached before terminating the process. The source will be useable in terms of acceptable $^3H$ emanation ratios whenever the tritium emanation ratio drops below unity. In addition, it is not necessary to continue the heat treatment at a particular temperature, for example 400° C, until the selected acceptable emanation ratio is reached, provided that the foil in use is to be operated at a lower temperature, for example 350° C, at which operating temperature the acceptable emanation ratio is not exceeded.

In a process for producing the radiation sources, the tritiated foils are obtained from the manufacturer with a specified amount of occluded tritium, such as 250 mCi$^3H$, and in batches of 200. All of these foils are placed together in a purgable chamber under good radiation safety conditions. The chamber is then heated to a suitable elevated temperature, for example, 300°–320° C, and left overnight, for example, 16 hours.

After this treatment, the tritium emanation level of the foils will have decayed to below the acceptable emanation ratio, which correlates to the arbitrarily set acceptable level at the desired upper limit operating temperature for the foils, for example, 340° C. The foils are then installed in the individual electron capture detectors during final assembly, and a spot check is made to determine the actual tritium emanation rate at the upper intended temperature of operation of the detectors.

I claim:

1. A method for analyzing the effluent of a gas chromatograph at temperatures above 300° C without exceeding an acceptable tritium emanation level, said method comprising the steps of:
   (a) heating a tritiated scandium $\beta$ particle source in a heatable vessel at a treatment temperature in excess of 250° C, said source initially exhibiting an unacceptable tritium emanation ratio at temperatures above 250° C, until the tritium emanation ratio of said source has passed through a maximum value;
   (b) heating the effluent of a chromatographic column to a temperature in excess of 300° C;
   (c) conducting said heated effluent to a zone in proximity with electrode means for creating a difference of electrical potential, said effluent being maintained at a temperature greater than 300° C;
   (d) removing said source from said vessel after the tritium emanation ratio of said source has passed through said maximum value, and disposing said source with respect to said zone in proximity with said electrode means so that $\beta$ particle emissions from said source can ionize said effluent; and
   (e) measuring the fluctuation in electron current as a function of time as said effluent passes through said zone in proximity with said electrode means.

2. A method for analyzing a gaseous effluent from a chromatographic column, the temperature of said effluent being higher than 300° C, said method comprising the steps of:
   (a) heating a tritiated scandium $\beta$ particle source in a heatable vessel at a treatment temperature in excess of 250° C, said source initially exhibiting an unacceptable tritium emanation ratio at temperatures above 250° C, until the tritium emanation ratio of said source reaches a value which correlates with an acceptable tritium emanation ratio at the temperature of said effluent;
   (b) maintaining a difference of electrical potential in an analyses region in the flow path of said effluent;
   (c) removing said source from said vessel after the tritium emanation ratio of said source has reached said value which correlates with an acceptable tritium emanation ratio at the temperature of said effluent, and disposing said source with respect to said analysis region so that $\beta$ particle emissions from said source can ionize said effluent; and (d) measuring any change in electron current in said analysis region as said effluent passes therethrough.

3. The method of claim 2 wherein the step of heating said tritiated β particle source at said treatment temperature is continued until the tritium emanation ratio of said source has passed through a maximum value.

4. The method of claim 2 wherein the step of heating said tritiated β particle source at said treatment temperature is continued until the tritium emanation ratio of said source reaches a value less than 1.